United States Patent [19]

Sundoro

[11] Patent Number: 4,680,338
[45] Date of Patent: Jul. 14, 1987

[54] BIFUNCTIONAL LINKER

[75] Inventor: Boby M. Sundoro, West Orange, N.J.

[73] Assignee: Immunomedics, Inc., Newark, N.J.

[21] Appl. No.: 788,284

[22] Filed: Oct. 17, 1985

[51] Int. Cl.$^4$ .......................... C07G 7/02; C08K 3/30; A61F 13/04

[52] U.S. Cl. .................... 525/54.1; 260/349; 260/350 R; 435/174; 436/532; 544/1; 544/179; 544/180; 544/224; 544/242; 544/336; 546/1; 548/541; 548/542; 548/543; 548/545; 548/546; 548/547; 548/551

[58] Field of Search .................. 525/54.1; 260/350 R, 260/349; 436/532; 435/174, 181; 544/1, 179, 180, 224, 242, 336; 546/1; 548/541, 542, 543, 545, 546, 547, 551

[56] References Cited

U.S. PATENT DOCUMENTS

| | | | |
|---|---|---|---|
| 4,237,229 | 12/1980 | Hartdegen et al. | 528/59 |
| 4,433,059 | 2/1984 | Chang et al. | 436/814 |
| 4,451,568 | 5/1984 | Schneider et al. | 435/181 |
| 4,544,683 | 10/1985 | Müller et al. | 524/4 |

Primary Examiner—Morton Foelak
Assistant Examiner—Nathan M. Nutter
Attorney, Agent, or Firm—Bernhard D. Saxe

[57] ABSTRACT

A selective bifunctional sequential linker has the formula

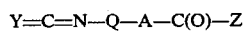

wherein Q is a homoaromatic or heteroaromatic ring system; A is a single bond or an unsubstituted or substituted divalent $C_{1-30}$ bridging group; Y is O or S; and Z is Cl, Br, I, $N_3$, N-succinimidyloxy, imidazolyl, 1-benzotriazolyloxy, OAr where Ar is an electron-deficient activating aryl group, or OC(O)R where R is —A—Q—N=C=Y or $C_{4-20}$ tertiary-alkyl. A method for activating an amine function towards reaction with a second amine involves reacting the amine with the foregoing linker. The resultant isocyanate or isothiocyanate derivative can then be reacted with a second amine to form a urea or thiourea conjugate.

The linker is useful for producing conjugates of ligands with amine-containing polymers and/or proteins, especially for forming antibody conjugates with chelators, drugs, enzymes, detectable labels and the like.

21 Claims, No Drawings

BIFUNCTIONAL LINKER

BACKGROUND OF THE INVENTION

The present invention relates to a selective bifunctional sequential linker and a method for using it to link two different amine-containing compounds. The method and linker of the invention are especially useful for preparing anitbody conjugates.

It is useful in a variety of situations to link a compound bearing a primary or secondary amine function to another compound bearing an amine function or another function. For example, a solid polymer support is often derivatized to form a pendant amine-containing polymer, after which it is linked to molecules of interest as components of an assay, e.g., an immunoassay. Such a polymer could also function as an immunoadsorbant for affinity chromatography.

Various bifunctional linkers can be used to achieve such linkages. Succinic anhydride converts an amine-functionalized polymer to a carboxyl-functionalized material, which can be reacted with another amine ligand using any of a variety of carboxyl activators, e.g., dicyclohexylcarbodiimide and its analogues. Alkylation of the amine with, e.g., N-succinimidyl bromoacetate (bromoacetic acid ester of N-hydroxysuccinimide) results in another carboxyl derivative which can be reacted with an amine or hydroxyl ligand to form an amide or ester. Acylation of the amine with N-acetyl-homocysteine thiollactone (5-acetamido-2-thiacyclopentanone) results in a derivative having a pendant thiol, which can be esterified or otherwise reacted to form an adduct.

Two immunoglobulins can be linked to form a cross-linked reagent useful as a component in an immunoassay, as disclosed in U.S. Pat. No. 4,433,059, the entire disclosure of which is incorporated herein by reference. In this application, one immunoglobulin was reacted at amine functions with an amine-reactive function on the linker, while the other immunoglobulin was reacted at thiol functions generated by cleavage of disulfide bonds or by deacetylation of S-acetylmercaptosuccinyl groups, the thiol function being reacted with, e.g., maleimide, iodoacyl or 2-pyridyldithio functions on the linker.

An amine-containing hapten can be linked to pendant amine groups of lysyl residues on an immunogenic protein to form an immunogen, as disclosed in, e.g., U.S. Pat. No. 4,486,344, which is incorporated herein in its entirety by reference. The linkers disclosed for this purpose were characterized as "phosgene equivalents", and included such reactive compounds as carbonyldiimidazole, disuccinimidyl carbonate, p-nitrophenyl chloroformate and the like. These reagents were generally used to form highly reactive intermediates, typically imidazoylureas, which were reacted in situ to form urea linkages with protein, which in this case was bovine serum albumin. The reference notes that such imidiazoylureas are normally not isolated, and it is doubtful whether it could be readily isolated and stably stored for any substantial period of time.

Diisothiocyanates are known as linkers for amine functions. However, formation of a monofunctional intermediate is complicated by significant addition at both isothiocyanate groups, unless a substantial excess of linker is used, which must then be removed prior to reaction with the second amine ligand.

A need therefore continues to exist for a selective bifunctional sequential linker which improves upon those known to the art.

OBJECTS OF THE INVENTION

One object of the present invention is to provide a selective bifunctional sequential linker for amine ligands which can form a stable, isolable intermediate with a first amine ligand without using a large excess of linker, and which can be reacted with a second amine ligand under mild conditions, and without reactivation of the functional group, to form a conjugate of the two amine ligands.

Another object of the invention is to provide a bifunctional linker which is especially useful in preparing antibody conjugates which are not appreciably cross-linked and which retain substantially the same immunoreactivity as the antibodies from which they are formed.

Upon further study of the specification and appended claims, further objects and advantages of this invention will become apparent to those skilled in the art.

SUMMARY OF THE INVENTION

These objects are achieved by providing a selective bifunctional sequential linker having the formula

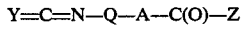

$$Y=C=N-Q-A-C(O)-Z$$

wherein Q is a homoaromatic or heteroaromatic ring system; A is a single bond or an unsubstituted or substituted divalent $C_{1-30}$ bridging group, Y is O or S; and Z is Cl, Br, I, $N_3$, N-succinimidyloxy, imidazolyl, 1-benzotriazolyloxy, OAr where Ar is an electron-deficient activating aryl group, or OC(O)R where R is $-A-Q-N=C=Y$ or $C_{4-20}$ tertiary-alkyl.

The invention further provides a method for activating an amine function towards reaction with a second amine by reacting the amine with the foregoing linker. The resultant isocyanate or isothiocyanate derivative can then be reacted with a second amine to form a urea or thiourea conjugate.

DETAILED DISCUSSION

It is preferred that the isocyanate (NCO) or isothiocyanate (NCS) group be bound to an aromatic ring to stabilize it. Thus, the aromatic ring system, Q, can be a homoaromatic or a heteroaromatic ring and/or a polynuclear aromatic ring system. Any of these aromatic ring systems will be substantially functionally equivalent to a benzene ring, although a benzene ring has practical advantages and is less likely to provoke side reactions during the processes of intermediate and conjugate formation or to produce untoward in vivo responses.

When Q is a benzene ring, which may be substituted with one or more substituents which do not interfere with the reaction, e.g., lower alkyl, lower alkoxy and the like. The NCO or NCS group will preferably be meta or para to the A group, since an ortho relationship would result in steric hindrance to conjugate formation.

Other aromatic systems (Q) which could be substituted for the benzene ring include, e.g., furan, pyridine and like mononuclear heterocycles, or naphthalene, benzofuran and the like di-, tri or polynuclear carbocyclic or heterocyclic aromatic ring systems any of which can be substituted with noninterfering substituents. The NCO or NCS group and the A group can be anywhere on these systems, but preferably not on adjacent, sterically hindered positions.

The group denoted by A can be a single bond joining the aromatic ring to the acyl function, or it can be a bridging group of up to 30 carbon atoms. The bridging group can be a straight or branched chain aliphatic, alicyclic or aromatic group and can be unsubstituted or substituted with noninterfering groups, e.g., halogen, hydroxyl, alkoxyl, preferably lower alkoxyl, nitro and the like. The group can also have one or more heteroatoms in place of carbon atoms in nonreactive positions. For example, an aliphatic chain can have one or more oxygen atoms in place of methylene groups, e.g., a polyoxyethylene bridge or the like. The bridging group can include alicyclic groups, e.g., cyclohexyl, cyclopentyl and the like, and/or aromatic groups, e.g., phenylene, furan and the like. Preferably, the acyl group is bound to the bridging group at a primary carbon atom, i.e., a $CH_2$ group, if the bridging group, A, is other than a single bond, for optimal reactivity and selectivity.

For practical reasons, primarily ease of preparation, A is preferably a single bond or a short aliphatic chain e.g., $C_nH_{2n}$ alkaline, where n is an integer from 1 to 6 (inclusive), preferably a straight chain, and more preferably methylene or ethylene.

The atom Y can be an oxygen atom or a sulfur atom, preferably a sulfur atom for better selectivity and stability of the intermediate amido-isothiocyanate.

The group Z is a reactive acyl derivative to achieve optimal selectivity of reaction with the first amine ligand. It can be a simple halide or pseudohalide such as $N_3$, or it can be an N-succinimidazyloxy, imidazolyl, 1-benzotriazolyloxy or OAr group, where Ar is an electron-deficient activating aryl group. Suitable such aryl groups include, e.g., nitrophenyl, dinitrophenyl and other groups having comparable electron-withdrawing properties to the foregoing. An electron-withdrawing effect on the oxygen of the OAr group at least as strong as that of m-nitrophenyl is desirable in order to achieve sufficient reactivity at the acyl group to selectively form an amide with the first amine-containing ligand without substantially any reaction with the NCO or NCS group of the linker.

The group Z can be OC(O)R, i.e., the linker can be an anhydride. It can be a symmetrical anhydride, wherein R is —A—Q—N=C=Y, or it can be a mixed anhydride, wherein R is a $C_{4-20}$ tertiary alkyl group, preferably t-butyl or t-amyl. Some advantages of a symmetrical anhydride are ease of preparation and crystallinity.

In terms of ease and economy of preparation, availability of starting materials, stability of intermediates and good selectivity, preferred linkers according to the invention are p-isothiocyanatobenzoyl chloride and p,p'-diisothiocyanatobenzoic anhydride. Other readily available and convenient linkers include the meta-analogues of the foregoing, the phenylacetic acid analogues and the phenylpropionic acid analogues.

Acyl bromides or azides can be substituted for acyl chlorides and may be advantageous where chloride-sensitive molecules or systems are involved or where it is desirable for some azide ion to be present, e.g., for bacteriostatic purposes. Certain O-linked or N-linked activating groups, e.g., N-succinimidazyloxy, imidazolyl, nitrophenyl esters, often confer crystallinity upon the linker, which is advantageous in handling.

In general, the linkers according to the invention are prepared from the corresponding amino carboxylic acids. These are either commercially available or readily synthesized using conventional synthetic pathways. Synthesis of other possible linkers will be well within the skill of the ordinary artisan.

Bridging groups (A) can be synthesized by conventional pathways, e.g., by building out from a methylaryl group, e.g., toluene, by oxidative reactions such as halogenation, oxidation and the like. Alternatively, benzyl halides, phenethyl halides and the like can be used as the starting materials for elaboration of longer bridging chains or groups by well-known chain extension reactions, e.g., Arndt-Eistert homologation, ethylene oxide additions, Michael additions, malonic ester alkylations, and the like.

Such reactions also include, e.g., linkage to the ring by acylation, alkylation, or reaction with an aralkylhalide, condensation with an aryl aldehyde or ketone or the like, or by reaction of an aryl or aralkyl Grignard reagent with an aliphatic or alicyclic aldehyde, ketone or ester, followed by appropriate oxidation/reduction or functional group transformations. A carboxy group can be masked, e.g., as an acetylene, added by addition of hydrogen halide to a double bond, followed by cyanide group displacement or other analogous conventional sequence, or generated by alkene oxidation, e.g., ozonolysis and oxidation.

Incorporation of alicyclic rings can be effected by, e.g., Diels-Alder reaction of butadiene with acrylic acid, followed by, e.g., addition of HBr across the double bond of the resultant cyclohexenecarboxylic acid, reaction with an acetoacetate, decarboxylation and reduction of the ketone carbonyl. The acetoacetate will normally be, e.g., a phenylacetoacetate or the like. Reduction of a ketone carbonyl can be effected concommitantly with nitro group reduction, using appropriate conventional hydrogenation catalysts.

Arylcarboxylic acids can be nitrated and the nitro group converted by chemical reduction or catalytic hydrogenation to an amine. For example, phenylacetic or phenylpropionate acid is readily nitrated e.g., with nitric/sulfuric acid mixture in nitrobenzene, to form predominantly the p-nitro derivative. Catalytic hydrogenation of this intermediate, e.g., with Raney nickel in ethanol, forms the p-amino acid.

The aminoaryl carboxylic acid can be converted to an isocyanato or isothiocyanato carboxylic acid chloride or acid by reacting it with an excess of phosgene or thiophosgene. (See, e.g., *J. Am. Chem. Soc.*, 68, 2506(1946). For example, an amino carboxylic acid is dissolved in strong aqueous acid, reacted with about one equivalent of thiophosgene, the reaction mixture is stirred until a precipitate appears, the crude product is filtered, washed with water, and crystallized to give an isothiocyanato carboxylic acid.

Preparation of isocyanatoacyl linkers is effected by reaction of an amino carboxylic acid with phosgene in an anhydrous solvent. General procedures for this conversion are well known, e.g., the procedure of Sandler et al., Ed., *Organic Functional Group Preparations*, Vol.1, 2d Ed., pp 364–365 (Academic Press, 1983); Cf., Hauser et al., *J. Org. Chem.*, 39, 1134 (1974). This reaction must be carried out in a well-ventilated hood! The reaction produces an isocyanatoacyl chloride.

The isothiocyanato carboxylic acid is conveniently converted to the acyl chloride with, e.g., oxaloyl chloride in a dry solvent, e.g., tetrahydrofuran (THF), at reflux. Displacement of the chloride with other acyl activating groups is effected by reaction with, e.g., a hydroxylic compound for esterification or an amine for activated amide formation. For example, a solution of an isothiocyanatoaroyl chloride is disolved in an anhydrous solvent, e.g., THF, dimethylformamide (DMF), dimethylsulfoxide (DMSO) or the like, and cooled to, e.g., ice bath temperature. A solution of, e.g., N-hydroxysuccinimide (about 1 equivalent), is added dropwise, then the bath is removed, and the reaction mixture is stirred for about another hour. The solvent is then evaporated to dryness to give a (normally) solid crude product which is generally suitable for immediate use to react with a first amine ligand. Phenols can be reacted as such or as their salts, e.g., alkali metal salts. A base, e.g., pyridine, sodium carbonate or the like, can be added to remove HCl generated in the reaction.

Reaction of the linker with a first primary or secondary amine-containing compound will normally be effected under substantially anhydrous conditions, e.g., in an anhydrous polar aprotic solvent, preferably dimethylformamide (DMF), dimethylsulfoxide (DMSO) or the like. A tertiary amine catalyst is advantageously added, e.g., pyridine, triethylamine or the like. Concentrations of about 1–1.1M for the linker, about 1M for the first amine-containing compound and about 1–2M for the catalyst are advantageously used, although these are merely convenient ranges and not limiting. It is convenient to dissolve the amine ligand and the catalyst in the solvent, cool these to the reaction temperature of about 0°–20° C., preferably 0° C., and add the linker as a solid or a solution in a minimum of solvent. The reaction mixture is stirred at the reaction temperature for an appropriate time, generally from 0.5 to 2 hours, preferably under an inert gas atmosphere, e.g., dry nitrogen or dry argon.

The intermediate isocyanate or isothiocyanate normally can be isolated as a stable solid. This normally can be accomplished by quenching the reaction with cold water, filtering the resultant suspension, and evaporating the filtrate to dryness in vacuo to recover crude product, which can be carried forward to the next step or further purified by conventional procedures.

Reaction of the NCO or NCS derivative with a second primary or secondary amine-containing compound will be effected under appropriate conditions depending upon the nature of the amine. In the case of a proteinaceous compound, containing a plurality of lysine residues, reaction is advantageously effected in buffered aqueous solution, in a pH range of about 8–10.5, preferably about 8.6–9.5. It may be necessary to dissolve the NC or NCS intermediate in an anhydrous aprotic solvent, e.g., DMF or DMSO, but the concentration of the aprotic solvent in the final aqueous solution should not be more than about 20% by volume, preferably not more than about 10% by volume. Substantially the same conditions can be used for conjugation to other amine ligands, e.g., aminodextrans, polylysine or the like. The resultant conjugate can be isolated by dialysis and lyophilization, and or purification by HPLC and/or column chromatography.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

Preparation of p-isothiocyanatobenzoyl chloride

A sample of p-aminobenzoic acid is dissolved in 3N HCl (20% by weight). To this is added about one equivalent of thiophosgene in a single portion. The reaction mixture is stirred until a white precipitate appears, the crude product is filtered, washed with water, and crystallized from acetone-water to give crude p-isothiocyanatobenzoic acid.

A sample of p-isothiocyanatobenzoic acid (1.0 g, 5.6 mmol) is treated with an excess of oxalyl chloride (20 ml) and refluxed under dry argon for 6 hours. After cooling, the unreacted oxalyl chloride is evaporated off in vacuo to give a crude white solid product (1.01 g, 90%), m.p. 72°–77° C.; IR (KBr): 2100, 1780 cm$^{-1}$; proton nmr (DMSO-d$_6$/TMS): δ 7.72 (4H AB quartet, ArH); Anal., Calc. for $C_8H_4NSOCL$: C 48.62, H 2.04, N 7.09; Found: c 49.02, H 2.11, N 7.09.

EXAMPLE 2

Preparation of p,p'-diisothiocyanatobenzoic anhydride

To a slurry of 4-isothiocyanatobenzoic acid (6.0 g, 33.5 mmol) in dry benzene (225 ml) is added thionyl chloride (10 ml). The mixture is refluxed under nitrogen for 24 hours, while water is removed using a Dan-Stark trap. The resultant hot benzene solution is filtered, cooled, and the resultant yellow crystals filtered and dried to give 2.12 g (20%) of product, m.p. 215°–216° C.; IR (KBr) 2110, 1780 cm$^{-1}$; proton nmr (CDCl$_3$): δ 7.75 (4H AB quartet, ArH); Anal. Calc. for $C_{16}H_8N_2S_2O_3$: C 56.46; H 2.37; N 8.23; Found: C 56.64; H 2.52; N 8.20.

EXAMPLE 3

Preparation of p-isocyanatobenzoyl chloride

Excess phosgene is bubbled through a solution of p-aminobenzoic acid (1 eqvt.) in dry, ethanol-free ethyl acetate, in the presence of 1-2 eqvts of imidazole, for about 30 min. Then the reaction mixture is gently boiled for about another 30 min, cooled, and the solvent is evaporated to dryness, to give a brown residue. Hot CCl$_4$ is then added, the insoluble urea by-product is separated by filtration, and the filtrate is evaporated under reduced pressure to yield the product, as an oil.

EXAMPLE 4

Preparation of N-(p-isothiocyanatobenzoyl)-deferoxamine

Deferoxamine (free base: 100.0 mg, 0.179 mmol) is dissolved in warm (65° C.) dry DMF. After cooling to 25° C., pyridine (43.0 mg, 0.536 mmol) and NaCl (31.0 mg, 0.531 mmol) are added. The mixtrue is cooled in a ice bath and solid 4-isothiocyanatobenzoic acid anhydride (40.0 mg, 0.118 mmol) is added at once. The reaction is stirred under argon at 0° C. for 1.5-2 hr and then quenched with water (203 ml) and filtered. The filtrate is evaporated to dryness to give white solids, washing several times with water (10 ml), THF (10ml) and dried to give white solids (76%): m.p. 176°–183° C.; IR (KBr): 2100 cm$^{-1}$; proton nmr (DMSO-d$^6$/TMS): δ 9.6 (3H, broad singlet), 8.1 (3H, broad singlet), 7.6–7.8 (4H, m), 2.2–3.5 (20H, m), 1.9 (3H,s), 1.2–1.5 (18H, m); Anal. calculated for $C_{44}H_{51}N_7SO_9$: C 54.91; H 7.12; N 13.58. Found: C 53.88; H 7.27; N 13.13.

EXAMPLE 5

Preparation of Deferoxamine-antibody conjugate

A sample (15 mg, $9.68 \times 10^{-8}$ mol)) of murine monoclonal anti-CEA IgG, in 900 ul of 0.1M sodium bicarbonate buffer, pH 9.0, containing 5% DMSO (by volume), is placed in an acid-washed glass vial and to it is added 100 ul of a solution of 35 mg isothiocyanatobenzoyldeferoxamine, prepared according to Example 4, in 1 ml dry DMSO (3.5 mg, $4.84 \times 10^{-6}$ mol), dropwise with constant stirring. The reaction is allowed to proceed at 37° C. for 3 hr, then the reaction mixture is centrifuged in a clinical table-top centrifuge at maximum speed for 10 min, and the supernatant is applied to a column of Sephadex G-50-80 ($1 \times 30$ cm), equilibrated with 0.1 N sodium acetate, pH 6.5, containing 0.15 N NaCl. The column is developed with the same buffer at a flow rate ot 25 ml/hr, and fractions of 0.75 ml are collected. The effluent is monitored by UV spectrometry at 280 nm and the fractions containing IgG are pooled, then sterile filtered into a sterile vial and stored at 4° C. until used. The coupling ratio obtained under these conditions is about 2 mol deferoxamine per mol IgG.

EXAMPLE 6

Preparation of Daunomycin NCS Derivative

Daunomycin hydrochloride (Sigma) (27.0 mg, 0.048 mmol) is dissolved in MeOH (5 ml) and to this is added a solution of sodium ethoxide (0.015 ml, 0.048 mmol). After a few minutes' stirring, the solvent is evaporated to dryness, anhydrous DMF (6 ml) is added, the solution is cooled in an ice bath, and solid 4,4'-diisothiocyanatobenzoic acid anhydride (16.3 mg, 0.048 mmol) is added. The mixture is stirred for an additional hour at ice bath temperature and the solvent is removed under reduced pressure. The residue is dissolved in chloroform (15 ml), washed twice with NaCHO$_3$, water and dried. The solvent is then removed to give solid (30 mg, 91%); m.p. 148°-153° C. (dec.); IR (CHCl$_3$) 2090 cm$^{-1}$; MS 711.47 (M+Na).

EXAMPLE 7

Preparation of Daunomycin-polylysine conjugate

To a solution of polylysine (Sigma, average m.w. 14,000, 5-10 mg) in DMSO (2 ml) and triethylene (2 drops) is added solid daunomycin-phenylisothiocyanate derivative prepared according to Example 6 (2-4 mg). The mixture is stirred at 25° C. for a period of 3-20 hours depending upon the number of molecules of daunomycin one may desire to conjugate to the polylysine. The reaction is then quenched with excess glycine and the daunomycin conjugate is separated by gel filtration using water as the eluent. The degree of substitution can be semiquantitatively determined by UV spectrometry at 495 cm$^{-1}$ using daunomycin.HCl as an external standard. The product can be isolated by lyophilization, or the aqueous gel filtration fractions can be used as such in subsequent reactions.

EXAMPLE 8

Preparation of Daunomycin-polylysine-antibody conjugate

The daunomycin-polylysine conjugate prepared according to Example 7 is acylated with N-succinimidyl m-maleimidobenzoate (MBS, N-hydroxysuccinimide ester of m-maleimidylbenzoic acid) (Pierce Chemical Co., Rockford, Ill.), using standard procedures, e.g., that of Kitigawa et al., *J. Biochem.*, 92, 585-590(1982). Antibody, e.g., murine monoclonal anti-CEA IgG, is thiolated with 2-iminothiolane (Sigma Chemical, St. Louis, Mo.), by standard procedures, e.g., that of Blatter et al., *Biochem.*, 24, 1517-1524(1985).

To 5 mM Bistris-acetate buffer, pH 5.8 (10-15 ml), NaCl (50 mM), and EDTA (1 mM), containing 10 mg of murine monoclonal anti-CEA IgG, was added a 5-25-fold excess of the daunomycinpolylysine conjugate prepared according to Example 7, in 100 mM sodium phosphate buffer, pH 7.0, containing EDTA (1 mM), at 0° C., after which is added 0.5M triethanolamine.HCl buffer, pH 8.0 (0.15 ml), to give a final pH of 7.0. The mixture is incubated at 0° C. for 2 hr, and then freshly prepared N-ethylmaleimide (1 mM) in ethanol (0.25 ml) is added to block any remaining free sulfhydryl groups on the antibody. After 30 min as 0° C., the solution is maintained on ice while concentrating to 10-12 ml using an immersible ultrafiltration unit (Millipore, CX-10 filter). The mixture is than applied to a 1.5 cm×60 cm column of Sephacryl S-300, equilibrated at 4° C. with 5 mM sodium phosphate buffer, pH 7.0, containing NaCl (15 mM) and NaN$_3$ (0.4 mM). Fractions of 1 ml volume are collected and analyzed by polyacrylamide SDS gel electrophoresis, similar fractions are pooled. The degree of substitution of daunomycin is measured quantitatively by UV spectrometry.

It will be apparent that other immunoglobulins can be used to make antibody conjugates, that other linkers can be used to join them to antibodies, and that other amine ligands can be used to form conjugates. It will also be apparent that other amines can be used for the second amine ligand to produce compounds wherein two amines are joined, other than the exemplified polylysine conjugates.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A selective bifunctional sequential linker having the formula

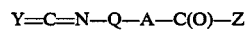

wherein Q is a homoaromatic or heteroaromatic ring system; A is a single bond or an unsubstituted or substituted divalent C$_{1-30}$ bridging group; Y is O or S; and Z is Cl, Br, I, N$_3$, N-succinimidyloxy, imidazolyl, 1-benzotriazolyloxy, OAr where Ar is an electron-deficient activating aryl group, or OC(O)R where R is —A—Q—N=C=Y or C$_{4-20}$ tertiary-alkyl.

2. The linker of claim 1, wherein A is a single bond.

3. The linker of claim 1, wherein A is a C$_n$H$_{2n}$ alkylene group, n being an integer from 1 to 6.

4. The linker of claim 1, wherein Z is Cl, Br or N$_3$.

5. The linker of claim 1, wherein Z is OC(O)R; and R is —A—Q—N=C=Y, t-butyl or t-amyl.

6. The linker of claim 5, wherein Q is meta- or paraphenylene; and A is a single bond or a $C_{1-6}$ alkylene bridge.

7. The linker of claim 1, wherein Z is N-succinimidyloxy, imidazolyl or 1-benzotriazolyloxy.

8. The linker of claim 1, wherein Z is OAr; and Ar is nitrophenyl or dinitrophenyl.

9. The linker of claim 1, wherein Q is meta- or paraphenylene.

10. The linker of claim 1, wherein Y is S.

11. The linker of claim 10 which is p-isothiocyanatobenzoyl chloride.

12. The linker of claim 10 which is p,p'-diisothiocyanatobenzoic anhydride.

13. A method for activating a first amine-containing compound having a primary or secondary amine function thereon towards reaction with a second amine-containing compound having a primary or secondary amine function thereon, comprising the step of contacting said first amine-containing compound with at least a stoichiometric equivalent of a selective bifunctional sequential linker having the formula $$Y=C=N-Q-A-C(O)-Z$$

wherein Q is a homoaromatic or heteroaromatic ring system; A is a single bond or an unsubstituted or substituted divalent $C_{1-30}$ bridging group; Y is O or S; and Z is Cl, Br, I, $N_3$, N-succinimidyloxy, imidazolyl, 1-benzotriazolyloxy, OAr where Ar is an electron-deficient activating aryl group, or OC(O)R where R is —A—Q—N=C=Y or $C_{4-20}$ tertiary-alkyl; thereby forming an amide bond to the acyl group of said linker and producing a resultant isocyanate or isothiocyanate derivative of said first amine-containing compound substantially without reaction with the N=C=Y group of said linker.

14. The method of claim 13, which further comprises the step of contacting said resultant isocyanate or isothiocyanate derivative with a second primary or secondary amine-containing compound; thereby forming a conjugate having at least one urea or thiourea linkage between said derivative and said second amine-containing compound.

15. The method of claim 14, wherein said second amine-containing compound is a protein containing a plurality of lysine residues.

16. The method of claim 15, wherein said protein is an immunoglobulin or a fragment thereof.

17. The method of claim 16, wherein said first amine-containing compound is deferoxamine.

18. The method of claim 17, wherein the isocyanate or isothiocyanate derivative of deferoxamine is isolated.

19. The method of claim 13, wherein Y is S.

20. A derivative of a primary or secondary amine-containing ligand, joined at the amine nitrogen, and having the formula $$Y=C=N-Q-A-C(O)\text{-amine}$$

wherein Q is a homoaromatic or heteroaromatic ring system; A is a single bond or an unsubstituted or substituted divalent $C_{1-30}$ bridging group; and Y is O or S.

21. A conjugate of a first primary or secondary amine-containing ligand and a second primary or secondary amine-containing ligand, each joined at the amine nitrogen, and having the formula $$\text{amine-}C(Y)NH-Q-A-C(O)\text{-amine}'$$

wherein Q is a homoaromatic or heteroaromatic ring system; A is a single bond or an unsubstituted or substituted divalent $C_{1-30}$ bridging group; and Y is O or S.

* * * * *